United States Patent [19]

Quang et al.

[11] Patent Number: 5,192,512

[45] Date of Patent: Mar. 9, 1993

[54] APPARATUS FOR PERFORMING CHEMICAL REACTIONS UNDER PRESSURE IN A MULTI-STAGE REACTION ZONE WITH EXTERNAL INTERMEDIARY THERMAL CONDITIONING

[75] Inventors: Dang V. Quang, Neuilly; Pierre Ham, La Celle Saint CLoud; Daniel Gelas, Croissy Sur Seine; Christian Legrand, Cergy, all of France

[73] Assignee: Institut Francais du Petrole, Rueil-Malmaison, France

[21] Appl. No.: 709,932

[22] Filed: Jun. 4, 1991

Related U.S. Application Data

[62] Division of Ser. No. 146,665, Jan. 21, 1988, Pat. No. 5,045,568.

[30] Foreign Application Priority Data

Jan. 27, 1987 [FR] France .................. 87 00751

[51] Int. Cl.⁵ .................................................. B01J 8/04
[52] U.S. Cl. ................................ 422/190; 422/192; 422/193; 422/198; 422/207; 422/212; 422/218; 422/220
[58] Field of Search ............ 518/706, 712; 422/190, 422/191, 192, 193, 194, 195, 207, 212, 218, 220, 198, 149

[56] References Cited

U.S. PATENT DOCUMENTS

| | | | |
|---|---|---|---|
| 1,719,610 | 7/1929 | Isenberg | 422/193 |
| 1,747,634 | 2/1930 | Isenberg | 422/193 |
| 2,271,646 | 2/1942 | Kassel | 422/191 |
| 2,306,011 | 12/1942 | Burk et al. | 422/191 |
| 2,322,366 | 6/1943 | Kaml | 422/193 |
| 3,010,807 | 11/1961 | Christensen et al. | 422/192 |
| 4,341,737 | 7/1982 | Albono et al. | 422/190 |
| 4,687,656 | 8/1987 | Quang et al. | 422/194 |

FOREIGN PATENT DOCUMENTS

| | | | |
|---|---|---|---|
| 1140071 | 1/1969 | United Kingdom . | |
| 2110105 | 6/1983 | United Kingdom | 422/218 |
| 2120119 | 11/1983 | United Kingdom | 422/193 |
| 2127321 | 4/1984 | United Kingdom | 422/192 |

Primary Examiner—Peter Kratz
Attorney, Agent, or Firm—Millen, White, Zelano and Branigan

[57] ABSTRACT

The invention concerns a process and an apparatus for performing chemical reactions under pressure in the presence of a solid catalyst in a multi-stage reaction zone, after external intermediary thermal conditioning. This process may be used for the synthesis of ammonia or methanol or for gasoline reforming. It is characterized in that at least one reaction fluid is introduced into at least one compartment, a first reaction effluent is recovered, a heat exchange takes place, outside the reaction zone, between a first effluent and an external heat exchange medium, then the first effluent is introduced into at least one subsequent compartment and a second reaction effluent is recovered from the subsequent compartment. The reaction fluid or reaction effluent circulates cross-wise in the compartments substantially perpendicularly to the reaction zone, the compartments being tight and of elongate shape, each compartment being adjacent to one or two other compartments, each group of two adjacent compartments comprising a common partition wall, either substantially parallel to generatrix or substantially oblique with respect thereto.

12 Claims, 3 Drawing Sheets

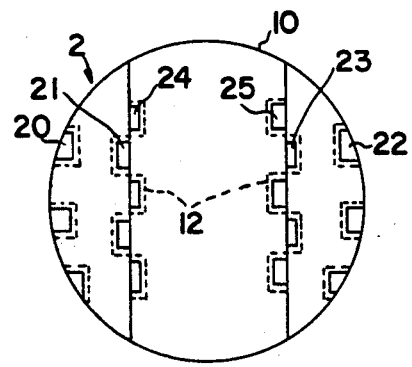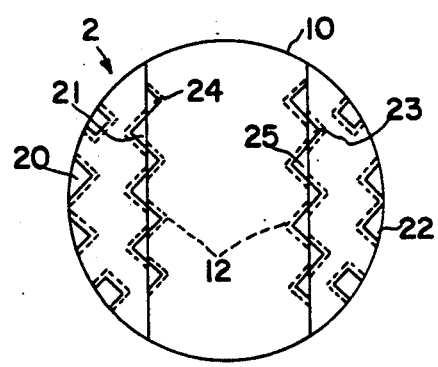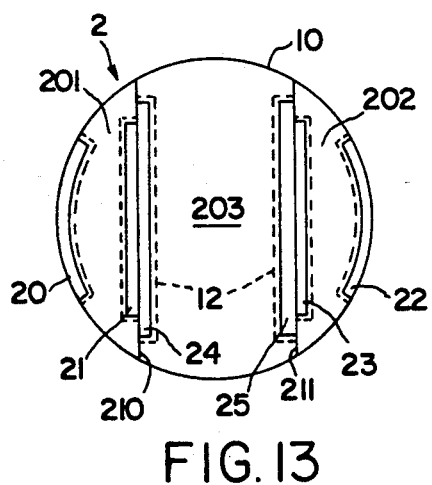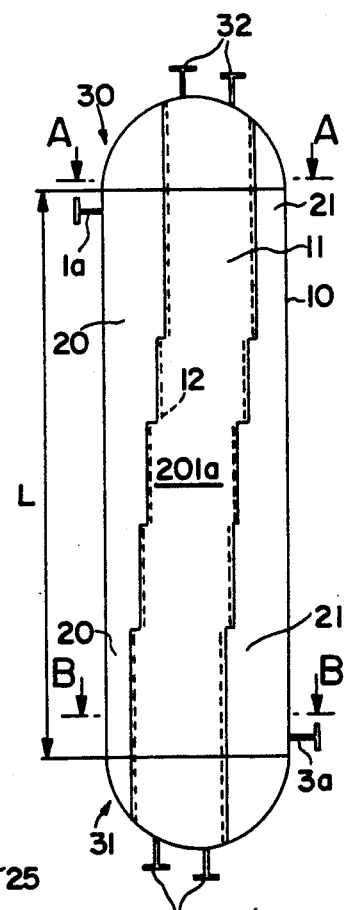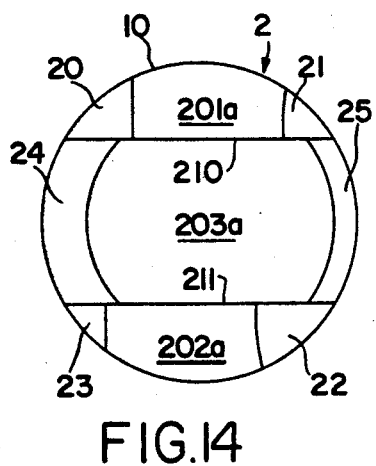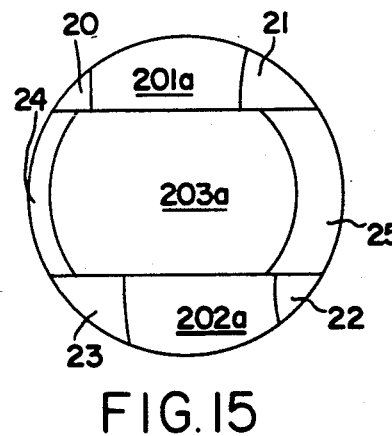

APPARATUS FOR PERFORMING CHEMICAL REACTIONS UNDER PRESSURE IN A MULTI-STAGE REACTION ZONE WITH EXTERNAL INTERMEDIARY THERMAL CONDITIONING

This is a division of application Ser. No. 07/146,665, filed Jan. 21, 1988, now U.S. Pat. No. 5,045,568.

The invention concerns a process for performing chemical reactions under pressure from reaction fluids in the presence of at least one solid catalyst, in a multi-stage reaction zone with external intermediary thermal conditioning. It also concerns a reactor for carrying out the process and the use of the reactor and of the process.

The invention may particularly be used for the synthesis of methanol, of ammonia, as well as for catalytic reforming, stabilizing hydrogenation of gasolines and hydrocracking of heavy oil cuts.

More generally, it is applicable to all processes using heterogeneous catalysis wherein fluid reactants, either in liquid or gas state or comprising both liquid and gas reactants, react with each other over successive catalyst beds formed of particles, granules, spherical solids or other solid elements or more or less complex and sophisticated structures.

BACKGROUND OF THE INVENTION

The concerned reactions generally develop reaction heat requiring one or more intermediary thermal adjustments with an external medium.

It is known that chemical reactions developing much heat may be performed in several steps with an intermediary thermal adjustment after each step.

Thus, the catalytic reforming of gasolines; for example; (see French Patent 2,160,269; U.S. Pat. No. 4,210,519; and U.S. Pat. No. 4,233,268) is usually conducted in three reactors with solid catalyst beds separated by two external heating furnaces.

The use of so many reactors is expensive in equipment, pipes and installation costs.

For this reason it has often be proposed to arrange the different reactors in a single reaction enclosure whose walls are adapted to withstand the relatively high internal pressure of the system.

For this purpose, the solid catalyst beds are vertically superposed and lay on supporting grids, or directly, on horizontal partition walls French Patent 2,573,996.

These grids and partitions must withstand both the weight of the catalyst bed and the strains resulting from the pressure drop generated by the flow of reaction fluid through heat-transfer elements and through the catalyst bed itself.

These two strains result in extremely high totals, on the order of 50–100 or even 150 tons per square meter, whereas the current specifications for industrial floors are limited to about 0.5–1 ton per square meter.

In order to avoid this cumulative strain effect resulting in constraining mechanical solutions as concerns as well the weight of the supporting beams as the lost dead space, it has been proposed, particularly for methanol reactors (Hydrocarbon Processing, May 1984: p. 95-100) to superpose reactors, not of the axial but of the radial type, where the catalyst is placed into a hollow cylindrical cartridge, or even into several cartridges, and the reaction fluid flows horizontally, either centrifugally from the internal cylinder to the external cylinder or centripetally from the external cylinder to the internal cylinder.

This solution has the advantage of releasing the separation floors from the strains due to the reaction fluid circulation, but has the disadvantage of leaving a large dead space, particularly a void central core which, according to British patent 1,140,071 can be used to house a heat exchanger.

A disadvantage of this solution, emphasized in U.S. Pat. No. 4,225,562 in the difficulty of accurately centering the two cylinders defining the ring of solid catalyst. A bad centering results in a heterogeneity of the fluid flow paths. Such a result is highly detrimental to good performance of the main reaction and results in excessive temperatures which are dangerous for the catalyst stability.

Another disadvantage is the requirement of charging and discharging catalyst cartridges. For this purpose, flanges of the same diameter as that of the reactor can be provided, but this is not the best solution when operating under pressure and with a reactor of large size. It is then recommended to weld the generally hemispherical end parts to the cylindrical body. But for each catalyst discharge operation it is necessary to saw off said end parts to withdraw the cartridges and to then weld back said parts again after the reactor phase of reactor charge. The operation is time-consuming, delicate and requires at each time administrative authorization and control.

On the other hand U.S. Pat. No. 4,225,562 teaches the provision of compartments after parallelpiped shaped as, arranged parallel to the enclosure axis. All of these compartments have the same sectional area and volume.

The device uses to the best one half of the available space. In addition to the mechanical complexity and the corresponding high cost of the device, the standardization of compartments of identical volume precludes the adaptation of the catalyst volume to the variation of the reaction velocity.

Consequently, the device according to this patent can be used only with reactors either of the single stage type, as far as kinetics is concerned, or performing reactions whose velocity is independent from the conversion rate, i.e., reactions of zero order.

Among the various embodiments of reactors with radial partitions, it is worth to mention the device disclosed in U.S. Pat. No. 3,898,049, wherein the catalyst cartridge is divided into tent 3 898 049, wherein several sectors in a longitudinal direction. The reaction fluids successively pass through these sectors, alternately downwardly and upwardly, in the direction of the reaction enclosure longitudinal axis. It is easily observed that the proposed device is only applicable in very peculiar circumstances where the travel lengths, and hence the pressure drops, are unimportant since, with reference to an axial reactor of same height and, a fortiori, to a radial reactor, the fluid travel is considerably extended in proportion to the number of sections of the cartridge.

The prior art is further illustrated by the British Patent 2 120 119 disclosing a longitudinal reactor for conducting chemical syntheses.in gas phase. This reactor comprises catalyst-containing parallelepiped enclosures arranged along the reactor axis and having permeable opposite walls through which the charge circulates. The effluent may be innerly cooled by quench, thus limiting the available internal space.

French Patent 2,573,996 illustrates a catalytic reactor with only one compartment for ammonia and methanol synthesis without internal heat exchanger. The wall temperature is maintained at a low level by the presence of an air space.

German Patent 2,929,300 discloses an exchanger reactor with axial flow through catalyst zones of variable cross-section, these zones being non-adjacent.

OBJECTS OF THE INVENTION

A first object of the invention is hence to provide a multi-stage process and reactor, operating under pressure with external intermediary thermal conditioning. A main object of the invention is to provide an inexpensive reactor, easy to manufacture and to operate for charging and discharging catalyst.

Another object is to provide a reactor where substantially the whole available volume may be occupied by the catalyst.

Still another object is to provide for a better control of the fluid velocity distribution through the catalyst beds so as to avoid local overheatings having the fatal effect of deactivating the catalyst and hence of decreasing the period of use and disturbing the reaction extent.

Other objects of the invention and further advantages thereof will be made apparent from the following description.

SUMMARY OF THE INVENTION

The invention concerns more particularly a process for conducting chemical reactions under pressure in a reaction zone comprising at least two compartments, each of which contains, at least partly, at least one solid catalyst wherein one reaction fluid is introduced into at least one compartment and circulates therethrough. A first reaction effluent from said compartment is recovered and heat is exchanged, outside of the reaction zone, between the first effluent and an external heat exchange medium. Said first effluent is then introduced after heat exchange with at least one subsequent compartment. Said first effluent flows through said subsequent compartment and a second reaction effluent is recovered from said subsequent compartment, said reaction zone being of elongate shape and comprising an enclosure with at least one generatrix, the process being characterized in that said reaction fluid, or reaction effluent, flows cross-wise through said compartments in a direction substantially perpendicular to said generatrix, said compartments being tight, of elongate shape in the direction of said generatrix, each of said compartments being adjacent to one or to two other compartments, each group of two adjacent compartments comprising a common wall, either substantially parallel to said generatrix or substantially oblique with respect to the latter.

In these conditions, the reactor offers a good compromise between filling and pressure drop level and further provides regular paths for the fluid through the catalyst bed.

Instead of a substantially oblique common wall, the reactor may have a wall comprising staggered sections in the same direction, each of them being parallel to the generatrix, but their assembly forming the equivalent of an oblique wall.

All these wall sections are so interconnected as to be fluid-tight. This characteristic offers the advantage of varying the catalyst bed thickness in the reactor to improve the fluid distribution within the catalyst mass over its whole height.

The reaction zone is advantageously cylindrical with circular base.

The length of each compartment and of each common wall is substantially that of the reaction zone and the cross-section of the compartment may be substantially inscribed in the section of the enclosure.

When the reaction zone (section of the enclosure) is advantageously circular, the cross-section of the compartments may be inscribed in the circle, defined by the section of the enclosure or in a circle coaxial therewith.

All the compartments are hydrodynamically insulated and tight so that no communication is possible between the various compartments inside the reaction zone, through any wall. The fluid or reaction effluent usually enters a compartment through a port connected to an inner distribution zone of the compartment and flows out therefrom after cross-passage in the whole catalyst bed, through an outlet connected to an inner collecting zone usually located at the opposite of the distribution zone.

The number of compartments and consequently of intermediary heat exchanges is variable. The section and/or volume of the compartments may be identical or different and is advantageously determined in accordance with the parameters and constraints of the process to be performed, for example, the reaction velocity which depends on the conversion advance rate.

The invention also concerns an apparatus for carrying out the process.

Generally, it comprises:

a reactor adapted to contain at least one catalyst, having a substantially cylindrical enclosure and comprising a first and a second tight end, at least two adjacent and tight compartments contained in said reactor, of elongate shape in the direction of said generatrix, each group of two adjacent compartments comprising a common wall, either substantially parallel to said generatrix or substantially oblique with respect thereof, each compartment further comprising at least one intake means for the reaction fluid or reaction effluent into said compartment and at least one outlet means for the reaction effluent having passed through said compartment, said intake and outlet means communicating with the reactor through said enclosure.

at least one distribution means in each compartment adapted to transversally distribute into each compartment the reaction fluid or reaction effluent substantially perpendicularly to said generatrix and connected to said intake means, at least one means for collecting the reaction effluent from each compartment, connected to said compartment outlet means, at least one heat transfer means interposed between said reaction effluent outlet means of one of the compartments and said reaction effluent intake means in the subsequent compartment.

Another transfer or heat exchange means consists, according to another embodiment, of using a mixture with a gas and advantageously with fresh and relatively cold fluid or reaction effluent for cooling the effluent at the outlet from a compartment and before its admission to the next compartment, with the advantage of saving one or more exchangers. For this purpose, the reactor is generally provided with intake means for this gas in order to produce said quench, said means being either inside or outside the reactor, preferably outside.

The reactor reaction zone, of elongate and preferably substantially cylindrical shape, is generally divided, along its length, advantageously in a direction substantially parallel to the generatrix, into several compartments, by means of tight partitions which may be directly connected to the enclosure casing. The length of the tight partition-walls along the generatrix is generally equal to the reactor length.

The reaction fluid, consisting either of a gas or a liquid or a gas-liquid mixture, passes successively through the so-defined compartments, previously filled with solid catalyst.

The fluid, more precisely the reaction effluent, after partial reaction over the catalyst bed of one of the compartments is discharged from the enclosure, passes through a heat transfer apparatus where it is brought to the adequate temperature and again penetrates the enclosure to pass onto the next catalyst stage. The volume of each compartment is generally so adjusted that, in each compartment, the difference between the compartment inlet and outlet temperatures is within the range from about 1 to 200° C. and preferably from 5 to 150° C.

This fluid passage generates pressure drops and pressure differences between the adjacent compartments of the enclosure. These dynamic pressure differences produce, on the compartment walls, mechanical strains which may be very high and may require excessive metal thicknesses.

The common walls of the different compartments, may consist of vertical or oblique supported planar panels, or advantageously of self-bearing panels of curved shape. They may be advantageously substantially parallel to the generatrix of the reaction zone.

When the panels are planar and supported, the supports preferably consist of stay-bars placed substantially perpendicularly to the planar panels and connected both to the partition wall and to the reaction enclosure.

When the panels are of the self-bearing type, they preferably comprise either assemblies of profiled sheets or cylindrical sectors, whose generatrices are substantially parallel to the reactor generatrix and whose bases are shaped either as arcs of circle of radius ranging from 0.1 to 100 times, preferably 0.5 to 50 times that of the reaction enclosure, or as portions of quadratic curves such parabolas, hyperbolas, or elipses.

Inside the compartments filled with solid catalyst elements, the reaction fluid or reaction effluent is introduced and distributed within the catalyst mass, through distributors forming the distribution zone.

The so-formed thin fluid jets, after passage through the catalyst bed, are collected and conveyed to the outlet by means of collectors generally located at the opposite of the distributors, which form the collecting zone.

The distributors and collectors are so arranged that the reaction fluid (and the effluent), instead of flowing in the longitudinal direction of the reaction zone, which considerably increases the travel of the fluids and the pressure drops resulting therefrom, flows perpendicularly to the axis of the cylinder forming the enclosure. The total travel of the fluid through the catalyst beds may generally be kept lower than twice the length L, from tangent to tangent, of the casing or cylindrical wall of the reaction zone, preferably at most equal to said length L (see FIG. 16, hereinafter defined).

For this purpose, the distributors and collectors may consist of pipes whose sections are either circles, sectors of circles, polygons or planes, or still sections commonly called "scallops". The area of the sections may vary along the generatrix in relation with the fluid flow rate at its level.

The pipes may be either parallel to the reactor generatrix or oblique with respect thereto.

Inlet and outlet means for the reactor fluid or the reaction effluent may be provided at any place in each compartment. However, they may be advantageously placed so that the inlet means is substantially located at the level of one of the reactor (or compartment) ends and the outlet means is located substantially at the level of the other end. According to this embodiment, the section of the distributing pipes at the inlet of the compartment is advantageously greater than that of the same distribution pipe at the other end of the compartment, in view of the greater gas flow rate at the inlet level and, conversely, the collecting pipe section is advantageously smaller at that inlet level, in view of lower flow rate of the gases collect at said level, than that of the same collecting pipe at the outlet end of the compartment.

By this arrangement, a substantially constant gas velocity can be maintained at any point of the distributor and of the collector, so that filling of the compartment with catalyst can be optimized.

For this purpose, according to a particular embodiment, the wall of the distributor and of the collector may comprise, on the parts facing the catalyst bed, at least one distribution or collecting section (a grid, for example) substantially parallel to the generatrix, or at least one distribution and collecting section substantially oblique with respect to said generatrix, each of said distribution and collecting sections being staggered in the same direction with respect to each other, so that the fluids pass through a constant thickness of Catalyst bed.

The number of distributors may be higher or lower than the number of collectors. Preferably, the number of distributors is the same as the number of collectors, so as to provide for a good distribution of the gas flow.

When only a few number, at most three, of distributors and collectors is used in a compartment, they may be placed against the enclosure, near the junction member between the enclosure wall and the common partition-walls. This solution is particularly advantageous when treating low flow rates and is very easy to perform. The flow of fluid and reaction effluent is then substantially parallel to the common partition-walls.

Preferably, when there are at least four distributors or collectors they are distributed along the common partition-walls and optionally on the enclosure wall parts facing said partition-walls. This arrangement provides for the treatment of high flow rates of fluid and of reaction effluent. It requires a circulation of fluid and of the reaction effluent substantially perpendicularly to the tight common partition-walls of the compartments.

For distributing or collecting the reaction fluid, the distributors and collectors may be either pierced with holes or consist of grids with openings formed between metal wires, either crossed or parallel, and whose profiles may be so determined as to obtain a maximum fluid flow.

In certain compartments, the average travel of a thin fluid jet from a distributor to a collector, or distance from the distributor to the collector may be identical for the different distributors, but this average travel of a fluid jet may vary from one distributor to another.

Preferably, the opening cross-sectional area on the catalyst bed of the distributor and of the collector facing it is variable in relation with the length of the average travel between these elements, i.e. the distance between the distributor and the collector facing it.

These different characteristics as well as other elements forming integral parts of the invention are described more in detail hereinafter.

According to one embodiment, the reaction fluid and the effluents may flow substantially parallel to the common partition wall defining two adjacent compartments, this being advantageous when the catalyst volumes are substantially of the same order in the different compartments.

According to another embodiment of the process, the reaction fluid and effluents circulate substantially perpendicularly to said wall, particularly when the distributors or collectors are located on said wall.

This embodiment is particularly advantageous when the catalyst volumes are very different in the different compartments.

The fluid velocity in the compartments, generally ranges from 1 to 200 m/s and preferably from 5 m/s to 100 m/s and, of course, depends on the selected reaction and operating conditions.

The temperatures of the fluids in the various compartments is generally from 100 to 800° C., preferably from 200 to 600° C.

BRIEF DESCRIPTION OF THE DRAWINGS

The invention will be better understood and its advantages made clearly apparent from exemplified embodiments described in relation with the accompanying drawings, whose figures diagrammatically illustrate, in a non-limitative manner, the apparatus and the process, and wherein:

FIGS. 7, 8, 9, 10, 11, 12 and 13 illustrate different types of distributors and collectors and different fluid and reaction effluent circulation modes;

FIGS. 14 and 15 show a partial cross-section of the reactor, substantially at the level of each end part thereof, along lines AA and BB; and FIG. 16 is a longitudinal cross-sectional view of the reactor.

In FIGS. 1A, 1B, 1C and 1D the same elements of the device according to the invention have been designated with the same reference number, respectively followed with letters a, b, c and d.

Figure 1A:
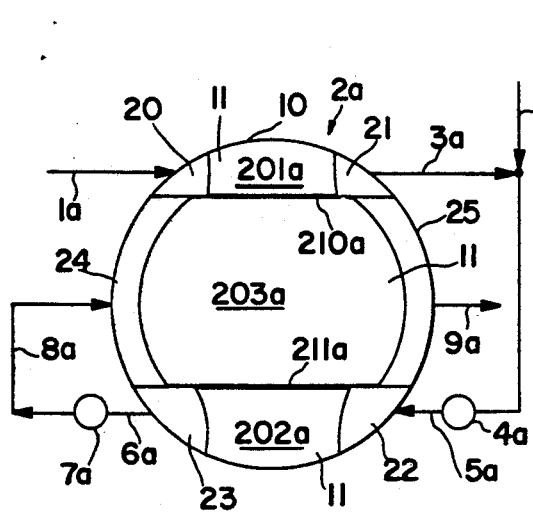
FIGS. 1A, 1B, 1C and 1D represent different embodiments of the process and of the reactor according to the invention.

For example, when using the apparatus according to the invention for methanol synthesis (FIG. 1A), a mixture mainly containing hydrogen and carbon oxides is supplied through the inlet pipe 1a to the top of reactor 2a containing a catalyst of the type of those disclosed in the book "Applied Industrial Catalysis" (Vol. 2, Chap. 6, p. 226 et sef.).

Reactor 2a, which is a vertical cylinder comprising a casing 10 of cylindrical section and circular base, closed at both ends by ellipsoid end parts or preferably by hemispherical end parts (30 and 31, FIG. 16) is divided into three compartments without internal communication, 201a, 202a and 203a, respectively of increasing volumes $V1 < V2 < V3$, by means of two internal tight plane walls (210a and 211a) which may be secured, for example, by welding to casing 10 and to end parts 30 and 31, arranged substantially parallel to the generatrix of reactor 2a.

The catalyst has been charged from the upper end part of the reactor into the various compartments. All of the cross-sections of the compartments are inscribed into the casing 10 of circular base.

Figure 8:
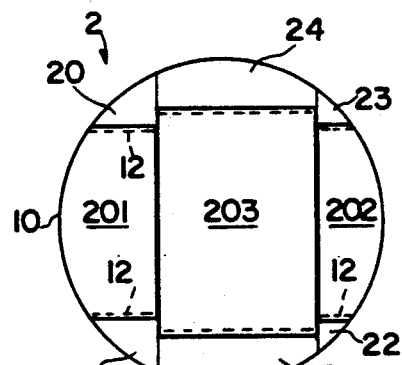

The reaction fluid, having a pressure and a temperature previously adjusted respectively to 8 MPa and to about 250° C., is introduced into compartment 201a substantially parallel to the common partition-wall, through at least one distributor 20 pierced with holes 12 (FIG. 8) generally scattered about its external wall facing the collector. In contact with catalyst 11 in the compartment, hydrogen combines with the carbon oxides to give methanol according to equations:

$$CO + 2H_2 \rightarrow CH_3 OH \qquad (1)$$

$$CO_2 + 3H_2 \rightarrow CH_3 OH + H_2O \qquad (2)$$

Reactions (1) and (2) are exothermic and, as the reaction progresses, the temperature of the fluid or of the reaction effluent increases.

When the temperature increase of the reaction effluent reaches 20 to 60° C., which corresponds to about 1-3% by volume of methanol present in the gas, the latter is withdrawn from compartment 201a through at least one collector 21 pierced with holes 12 (FIG. 8) or of the grid type and conveyed through line 3a of the lower part towards a known, per se heat transfer means, 4a e.g. an external cooler, which brings it back substantially to its initial temperature at which it was fed to 201a. Instead of a heat exchange at 4a, a quench may be performed by means 4f for introducing at least a part of the reaction fluid or of the cold effluent into the line conveying the effluent to the next compartment.

From cooler 4a, which may be either an air-cooler or a heat-recovery apparatus preheating for example all or a part of the charge or producing hot water or steam under pressure, the gas mixture is fed, through line 5a, to the top of reactor 2a where it is introduced, through at least one distributor 22, into compartment 202a, symmetrically opposite to compartment 201a.

When, as a result of the reaction, the gas temperature is again increased by 20-60° C. above its intake temperature, the reaction effluent is again withdrawn through at least one collector 23 in the lower part of the reactor, conveyed through line 6a to cooler 7a which again brings it back to the initial optimum temperature. From 7a, the fluid flows through line 8a to the upper part of the reactor to reach compartment 203a of reactor 2a through at least one distributor 24.

At the outlet from 203a, the mixture, which finally contains from 2 to 12% by volume of methanol, is fed, through collector 25 and line 9a, into the lower part of the reactor, to the unit for condensation and purification of the synthesized alcohol.

According to said FIG. 1A , the fluid and the reaction effluent flow cross-wise, substantially perpendicular to the reactor generatrix and parallel to the common partition-walls.

Compartments 201a, 202a and 203a may be placed side-by-side, compartment 202a being in central position. Said order minimizes the strains resulting from the pressure differences applied onto the common partition-walls 210a and 211a.

In a preferred arrangement, the last compartment 203a (FIG. 1A) is in central position between the two first compartments 201a and 202a.

As a matter of fact, comparative surveys have shown that this arrangement is the most favorable for optimizing the available effective space.

In the above description (FIG. 1A) the reactor 2a is placed vertically.

Figure 1B:
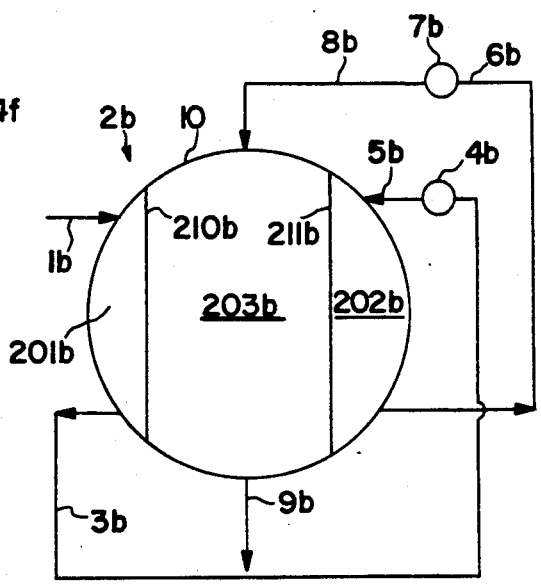

Depending on the local requirements, for example, when the ground is spongy and soft, reactor 2 may be arranged horizontally according to another embodiment, as illustrated in FIG. 1B.

In this alternative embodiment, lines 1b, 3b, 5b, 6b, 8b and 9b are preferably so arranged that the reaction fluid flows downwardly substantially parallel to the common partition-wall, thus avoiding the risk of destabilization of the catalyst bed by blowing of the catalyst particles.

Figure 1C:
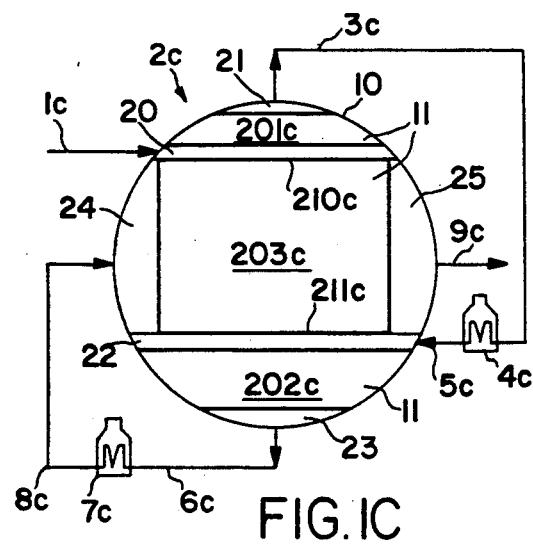

FIG. 1C, illustrating another embodiment, shows a reaction system for gasoline catalytic reforming, which is endothermic. The diagram simultaneously illustrates an where the fluid and the reaction effluent flow perpendicular to walls 210c and 211c, in compartments 201c and 202c, and where they flow parallel to said same walls in compartment 203c.

Through line 1c, naphtha vapors and recycled hydrogen circulate. The gas and naphtha vapor mixture is previously conditioned at about 0.5-3 MPa and about 500-530° C. In compartment 201c of reactor 2c, the reforming catalyst, which may consist of platinum deposited on acid carrier and doped with other noble metals such as for example, rhenium, is used to subject naphtha essentially to dehydrogenation reactions which strongly decrease the temperature of the reaction fluid to about 450-480° C. This fluid is then removed from compartment 201c and conveyed through line 3c to the external furnace 4c, of known type, where it is heated to about 500° C.

The fluid is then supplied through line 5c to compartment 202c. In compartment 202c, in addition to dehydrogenation, molecule rearrangement reactions are performed and the temperature decrease is much less substantial.

When said temperature decrease reaches about 10 to 30° C., the fluid flows out from the second compartment 202c and is again heated to about 500° C. in furnace 7c.

The third compartment 203c is substantially isothermal. As a matter of fact, in addition to the dehydrogenation and molecular rearrangement reactions hydrogenation reactions occur which are exothermic and the reaction heat thereof compensates for the heat loss due to reforming proper.

The processes of the invention according to FIGS. 1A, 1B and 1C are applicable to reactors in which different compartments are serially connected, so as to form a succession of, stages, in the kinetic meaning of the word.

They also apply to multi-stage reactors, some compartments of which may be connected in parallel (FIG. 1D) to form together either the first or the last reaction stage.

This particular embodiment may be advantageous for certain reactions, particularly for ammonia synthesis.

As a matter of fact, it is known, at present, to operate this synthesis under relatively mild conditions (pressure of about 10 MPa and temperature of about 400° C.) an , in these conditions, it is no longer necessary to provide a double jacket for cooling the external wall of the reaction enclosure.

However, for these reactors without wall cooling, called "hot-wall reactors", difficulties arise due to the pressure drops resulting from the large volume of gas flowing through the catalyst bed.

By dividing the gas flow rate by two at critical locations, this difficulty can be evaded.

Figure 1D:
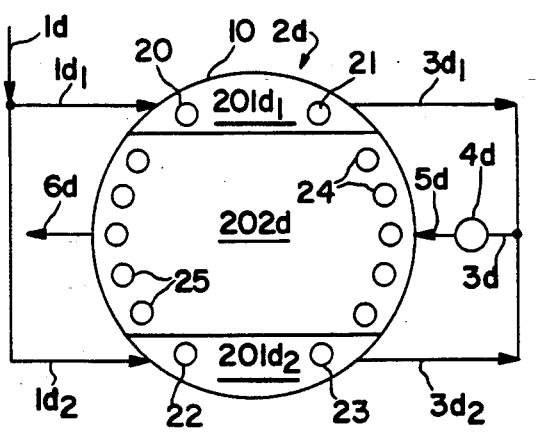

FIG. 1D diagrammatically shows a reactor for ammonia synthesis, built in conformity with the process of the invention.

A mixture of synthesis gases containing about 25% nitrogen, 75% hydrogen and ammonia and argon traces (<5%) are introduced under about 10 MPa and at 350-400° C. through line 1d. Line 1d is extended by two lines 1d1 and 1d2 conveying said gas into the two compartments 201d1 and 201d2, advantageously of equal volumes and of equal sections, symmetrically arranged with respect to the axis of the cylinder defining the reaction volume.

Due to this parallel connection, the volume of said first catalyst stage, although small with respect to the volume flow of the synthesis gas, finally offers only little resistance to the gas flow.

At the outlet of compartments in parallel 201d1 and 202d2, the synthesis gas contains about 4-7% of ammonia and its temperature is increased by about 40-60° C.

Gases flowing through lines 3d1 and 3d2 are supplied through line 3d to exchanger 4d, for heat recovery.

At the output of exchanger 4d, the gases, cooled at the optimum temperature of about 350-400° C., are conveyed through line 5d to the central compartment 202d of reactor 2d.

The effluent gases from reactor 2d, which contain about 8 to 14% by volume of ammonia approximately at a temperature of 400-450° C. and under a pressure of about 10 MPa, are fed through line 6d to the ammonia conditioning and recovery unit placed after the reaction section.

In the described reactors (FIGS. 1A, 1B, 1C) the partition-walls 210 and 211, although released from the weight of the catalyst, directly laying onto the enclosure wall, have to nevertheless resist generally the thrust resulting from the pressure difference between adjacent compartments 201-203 on the one hand, 203-202 on the other hand.

These pressure differences are due to the pressure drop through the catalyst beds and the heat transfer apparatuses and are on the order of 0.1-0.4 MPa. They may even reach 1 MPa when using heating furnaces as, for example, in reforming operations.

In the example of methanol, synthesis reactor, shown in FIG. 1A, the wall 210a (for example) of 3200 mm width and 20 mm thickness, is designed to resist to a pressure difference of 0.3 MPa.

Figure 2:
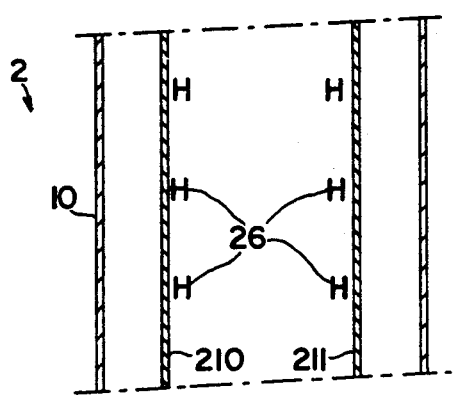
FIGS. 2, 3, 4, 5 and 6 show different types of tight common partition-walls.

When using a bearing system parallel to the plane of said wall, beams of HEM 400 type, distributed every 500 mm (FIG. 2) are convenient.

Figure 3:
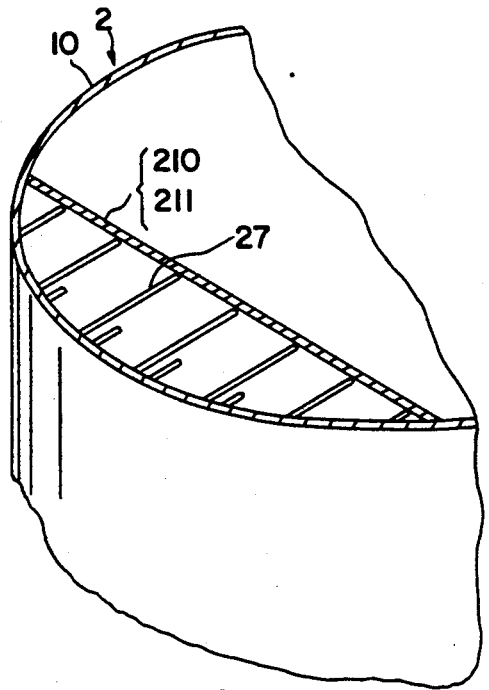

With a perpendicular bearing system, stay-bars of 25 mm diameter, arranged in square mesh pattern of 500 mm side, can be used, for example. These stay-bars are connected to the partition-walls 211 and to the wall of the reaction enclosure 10 (FIG. 3).

The planar wall with its relatively bulky bearing systems difficult to fix, may be replaced by a simple wall of special shape, so designed as to alone withstand the pressure.

Figure 4:
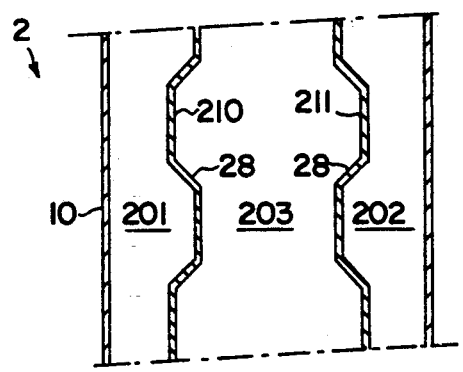

When using a self-bearing form, the profiles may have the same thickness, for example, as that of the planar wall 210a (20 mm) of the type shown in FIG. 4 with a height of, for example, 300 mm and a pitch of 395 mm.

Figure 5:
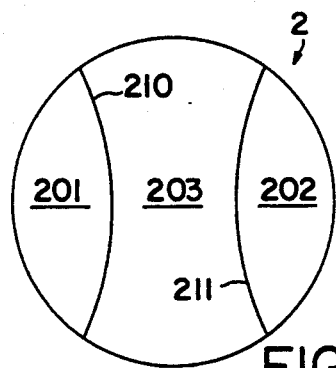
Figure 6:
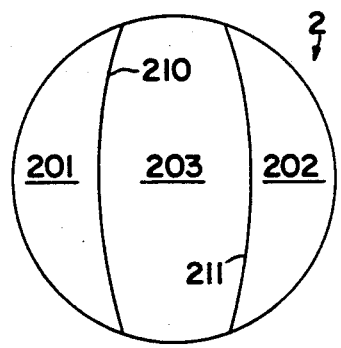

FIGS. 5 and 6 show other self-bearing forms according to the invention with convex and concave sides oriented towards compartments 201 and 202. A combination of these various forms may also be used. These forms are preferred to those shown in FIG. 4 since they facilitate the connection between these walls and the wall of the cylindrical reactor.

The walls 210 and 211 are cylinder sectors whose generatrices are substantially parallel to the generatrix of the reaction enclosure and whose bases are arcs of circle of radius ranging from 0.1 to 100 times, preferably 0.5 to 50 times that of the reaction enclosure.

In the reactors according to the invention, the reaction fluids flow cross-wise, perpendicular to the enclosure generatrix. Accordingly, distributors 20, 22, 24 and collectors 21, 23, 25 are preferably formed of pipes substantially parallel to said generatrix, whose openings 12 are generally scattered about their walls in the direction of the catalyst bed.

Figure 7:
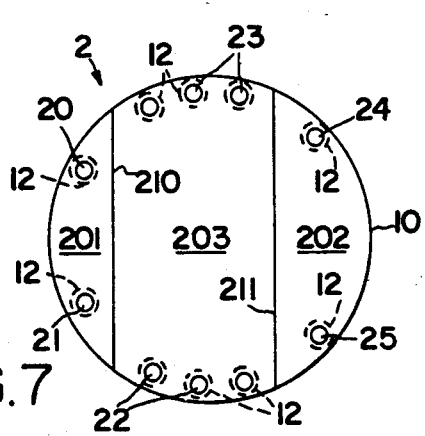
Figure 9:
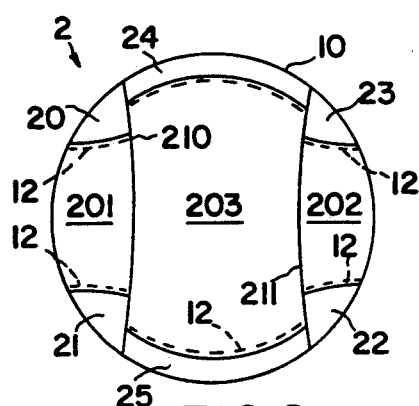

Preferably, the cross-section of the distribution (20, 22, 24) and/or collecting (21, 23, 25) pipes may be shaped as shown in the figures, either as a circle (FIG. 7) or as a sector formed at the junction between the reactor wall and the common partition wall and closed by a plane (FIG. 8) or by a cylinder portion of circular base (FIG. 9), the fluids then flowing substantially parallel to the common partition-walls.

Figure 10:
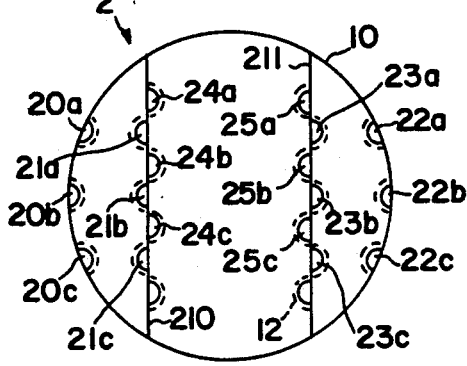

When the total cross-section of the distributors or of the collectors amounts to more than 10%, preferably more than 20% of that reserved for the catalyst, distributors 20, 22, 24 and collectors 21, 23, 25 preferably consist of several pipes (FIGS. 10, 11 and 12) substantially parallel and distributed along the common partition-wall 210 and optionally along the part of the reaction enclosure wall 211 facing it; the flow direction is then substantially perpendicular to the common partition-walls.

These different distribution pipes 20a, 20b, 20c ... of the first compartment, 22a, 22b, 22c ..., of the second compartment and 24a, 24b, 24c ..., of the third compartment, as well as the different collecting pipes 21a, 21b, 21c ..., 23a, 23b, 23c ..., 25a, 25b, 25c, respectively of the first, second and third compartments, may be shaped as sectors of circle (FIG. 10) or of polygones, for example triangles (FIG. 12), or squares or rectangles (FIG. 11). In the embodiment illustrated in FIG. 11, the number of distributors 24 is lower than the number of collectors 25, but conversely, a reactor could have been built as well with a number of collectors lower than the number of distributors.

FIG. 13 shows another embodiment of distributors and collectors shaped either as an arc of circle 20, 22 close to the casing, or plane 21, 23, 24, 25 close to the common partition-walls 210 and 211.

According to these various embodiments, a larger cross-section of openings 12 compensates for the lower number of distributors or collectors.

The openings 12 for introducing and collecting fluids may be of any shape, for example circular, and their cross-sectional area is advantageously proportional to the average travel corresponding to each distributor-collector pair so as to minimize the preferential passages of the gases.

As shown in FIGS. 14, 15 and 16, illustrating an embodiment of the distribution and collecting means, the line 1a of FIG. 1A is substantially placed at the level of one of the end parts 30 of the reactor or of the first compartment 201a, whereas the output line 3a is placed substantially at the level of the other end part 31 of the reactor or of the first compartment. The cross-section of the distribution duct, for example 20, in compartment 201a, at the level of end part 30 (FIG. 14, AA-cut) is greater than at the level of end part 31 (FIG. 15, BB-cut) whereas the cross-section of collecting duct 21 at the level of end part 30 is smaller than that of collecting duct 21 at the level of end part 31. The same is true for the sections of the other distribution ducts 22, 24 and collecting ducts 23, 25 in the other compartments (FIG. 14, 15).

According to FIG. 16, illustrating more particularly this embodiment, the walls of distributor 20 and collector 21 facing the catalyst bed, may comprise sections (grids with holes 12, for example) substantially parallel to the generatrix and staggered with respect to one another in the same direction, so that the thickness of the bed traversed by the fluids is the same all along the reactor and said walls are oblique as a whole with respect to the generatrix.

The operations of charging the catalyst may generally be performed through at least one opening 32 in the upper end part of the reactor and preferably through at least one opening per compartment. For horizontal reactors with vertical common partition-walls 210b and 211b (FIG. 1B), the catalyst may be charged through openings generally provided in the reactor casing at the level of each compartment.

The catalyst is generally discharged from the bottom through at least one exhaust port 33 and preferably through one port in each compartment. These charging and discharging operations are easily performed and thus the reactor did not stand idle for a long time.

The reactor walls (those of the casing and of the common partitions) may be heat insulated. An intermediary fluid, introduced for heating or cooling, may optionally circulate within the partition-walls, particularly the common partition-walls of adjacent compartments.

The above-figures only show a reactor with three compartments and two heat-transfer means, for sake of clarity. Obviously, it is possible to build a reactor according to the invention having a plurality of compartments, for example 3 to 10 and of intermediary heat-transfer means.

What is claimed is:

1. An apparatus for conducting chemical reactions, comprising:

a reactor of elongated shape containing at least one catalyst bed, said reactor comprising a substantially cylindrical casing having a generatrix, and first and second tight end parts;

at least two tight adjacent compartments contained in said reactor of elongated shape, said compartments extending lengthwise, in the direction of the generatrix, along substantially the entire length of said reactor;

each group of two adjacent compartments having a common partition-wall, said common partition-wall having a longitudinal axis which is either substantially parallel to said generatrix or substantially oblique with respect thereto, said common partition-wall being in fluid tight connection with said casing, and each of said compartments having a first end and a second end opposite said first end;

each compartment further comprising at least one inlet means located at said first end for introduction of fluid into said compartment and at least one outlet means located at said second end for removal of fluid which has passed through said compartment, said inlet and outlet means being in fluid communication with the exterior of said reactor through said casing;

at least one distribution means in each of said compartments for crosswise distributing fluid in a direction substantially perpendicular to said generatrix, said at least one distribution means being in fluid communication with said at least one inlet means;

at least one collecting means in each of said compartments for removing fluid therefrom, said at least one collecting means being in fluid communication with said at least one outlet means, whereby fluid introduced into each of said compartments via said at least one inlet means is distributed by said at least one distribution means, traverses said compartment from said first end to said second end, is collected by said at least one collecting means, and is removed by said at least one outlet means; and at least one heat transfer means interposed between said at least one outlet means of one of said compartments and said at least one inlet means of another of said compartments, said at least one heat transfer means being external to said casing.

2. An apparatus according to clam 1, wherein said cylindrical casing has a base of circular section.

3. An apparatus according to claim 1, wherein said common partition-wall comprises planar panels.

4. An apparatus according to claim 1, wherein said common partition-wall comprises self-bearing panels of curved shape.

5. An apparatus according to claim 4, wherein the base of the self-panels of curved shape is shaped as an arc of circle of radius ranging from 0.1 to 100 times that of the reactor, or is shaped as a portion of a quadratic curve.

6. An apparatus according to claim 1, wherein said distribution means and said collecting means are arranged substantially parallel to said generatrix in each compartment.

7. An apparatus according to claim 1, wherein said inlet and outlet means are respectively located proximate to said reactor first end part and said reactor second end part, each of said at least one distribution means and at least one collecting means extending lengthwise in the direction of said generatrix, the cross-sectional area of said at least one distribution means, proximate said reactor first end part, being larger than the cross-sectional area of said at least one distribution means proximate said reactor second end part, and the cross-sectional area of said at least one collecting means proximate said reactor first end part being smaller than that of said at least one collecting means proximate said reactor second end part.

8. An apparatus according to claim 7, wherein said at least one distribution and at least one collecting means of each of said compartments comprising, respectively, more than one distribution or more than one collecting sections, each of said sections being substantially parallel to said generatrix or substantially oblique with respect to said generatrix, each of said sections having an axis, the axis of each of said distributing sections being out of line with respect to one another, and the axis of each of said collecting sections being out of line with respect to one another.

9. An apparatus according to claim 1, wherein each of said distribution means having means defining a plurality of fluid outlets arranged along the length of said distribution means, and each of said collecting means having means defining a plurality of fluid inlets arranged along the length of said collecting means.

10. An apparatus according to claim 1, wherein said reactor is horizontal and comprises at least one substantially vertical common partition-wall.

11. An apparatus according to claim 1 comprising cold gas feeding means interposed between said outlet means of one of said compartments and said inlet means of another of said compartments.

12. An apparatus for conducting chemical reactions, comprising:

a reactor of elongated shape containing at least one catalyst bed, said reactor comprising a substantially cylindrical casing having a longitudinal axis and first and second tight end parts;

at least two adjacent compartments contained in said reactor of elongated shape, said compartments extending lengthwise, in the direction of said longitudinal axis, along substantially the entire length of said reactor, each group of two adjacent compartments comprising a common partition-wall, said common partition-wall having a longitudinal axis which is either substantially parallel to said longitudinal axis of said casing of substantially oblique with respect thereto, said common partition-wall being in fluid tight connection with said casing, and each of said compartments having a first end and a second end opposite said first end;

each compartment further comprising at least one inlet means located at said first end for introduction of fluid into said compartment and at least one outlet means located at said second end for removal of fluid which has passed through said compartment, said inlet and outlet means being in fluid communication with the exterior of said reactor through said casing;

at least one distribution means in each of said compartments for cross-wise distributing fluid in a direction substantially perpendicular to said longitudinal axis, said distribution means being in fluid communication with said at least one inlet means;

at least one collecting means in each of said compartments for removing fluid therefrom, said at least one collecting means being in fluid communication with said at least one outlet means, whereby fluid introduced into each of said compartments via said at least one inlet means is distributed by said at least one distribution means, traverses said compartment from said first end to said second end, is collected by said at least one collecting means, and is removed by said at least one outlet means; and at least one heat transfer means interposed between said at least one outlet means of one of said compartments and said at least one inlet means of another of said compartments.

* * * * *